(12) United States Patent
Su et al.

(10) Patent No.: US 7,232,921 B2
(45) Date of Patent: Jun. 19, 2007

(54) METHOD FOR PREPARING A BIPHENYLPHOSPHONATE COMPOUND

(75) Inventors: Wen-Chiung Su, Taipei (TW); Chin-Shang Sheng, Longtan Township, Taoyuan County (TW)

(73) Assignee: Chung Shan Institute of Science & Technology, Taoyuan (TW)

( * ) Notice: Subject to any disclaimer, the term of this patent is extended or adjusted under 35 U.S.C. 154(b) by 375 days.

(21) Appl. No.: 10/972,396

(22) Filed: Oct. 26, 2004

(65) Prior Publication Data

US 2005/0101793 A1 May 12, 2005

(30) Foreign Application Priority Data

Nov. 12, 2003 (TW) .............................. 92131729 A

(51) Int. Cl.
C07F 9/02 (2006.01)
(52) U.S. Cl. ........................................................ 558/82
(58) Field of Classification Search ................... 558/82
See application file for complete search history.

(56) References Cited

U.S. PATENT DOCUMENTS 6,440,891 B1 * 8/2002 Maas et al. ................. 502/162

\* cited by examiner

*Primary Examiner*—Joseph K. McKane
*Assistant Examiner*—Rei-tsang Shiao
(74) *Attorney, Agent, or Firm*—Bacon & Thomas PLLC

(57) ABSTRACT

A method for preparing a biphenylphosphonate compound of the following formula (I):

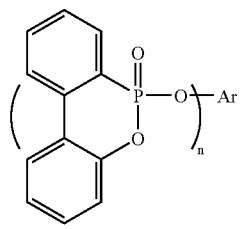

(I)

wherein n is 2 or 3; Ar is a $C_6$–$C_{16}$ aromatic group; which comprising (a) reacting an o-phenylphenol with a phosphorus trichloride in the presence of a zinc chloride catalyst to form a 6-chloro-6H-dibenz [c,e][1,2] oxaphosphorin of the following formula (II);

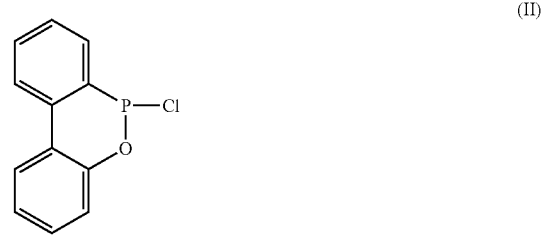

(II)

(b) reacting a polyhydroxybenzene compound of the formula (III)

$(HO)_n$—Ar  (III)

wherein n and Ar are defined the same as the above, with the compound of formula (II) to form a compound of the following formula (IV)

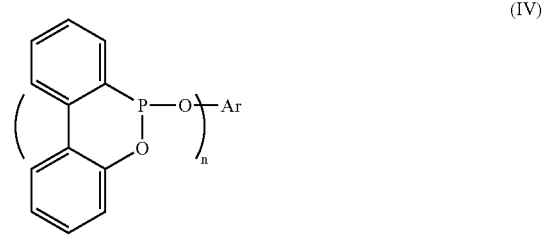

(IV)

wherein n and Ar are defined the same as the above; and (c) oxidizing the compound of formula (IV) in the presence of water and ozone to form the compound of formula (I).

7 Claims, No Drawings

METHOD FOR PREPARING A BIPHENYLPHOSPHONATE COMPOUND

BACKGROUND OF THE INVENTION

1. Field of the Invention

The present invention relates to a method for preparing biphenylphosphonate compound, and is particularly about the production of biphenylphosphonate compound used as a type of flame retardant.

2. Description of the Related Prior Art

Biphenylphosphonate compound were commonly used as a type of flame retardant for processing plastic products manufactured at high temperature. The most well-known flame retardant phosphate compound is tetraphenyl resorcinol diphosphate (RDP), which could be prepared by various methods, such as esterification using magnesium chloride, zinc chloride, or aluminum trichloride as catalyst. But the low selectivity and mono-condensed side products have been the downside of RDP compound.

The inventor of the present invention had disclosed a preparation method for a type of aromatic phosphonate compound under Taiwan Patent No. 143,835, but the reaction yield was excessively low. To simplify the reaction procedure and improve the reaction yield, the present invention has come out with better method for the production of biphenyl-phosphonate compound.

SUMMARY OF THE INVENTION

The object of the present invention is to provide a method for the preparation of biphenylphosphonate compound with simplified procedure and higher yield.

The present invention provides methods for preparing the biphenylphosphonate compound of the following formula (I)

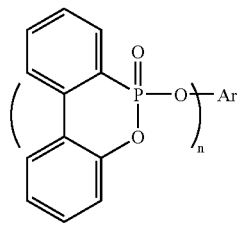

wherein n is 2 or 3; Ar is $C_6$–$C_{16}$ aromatic group.

Method 1

The compound of formula (I) can be prepared by the following steps of (a), (b), and (c):

(a) reacting o-phenylphenol with phosphorus trichloride in the presence of zinc chloride catalyst to form a 6-chloro-6H-dibenz [c,e][1,2] oxaphosphorin of the following formula (II);

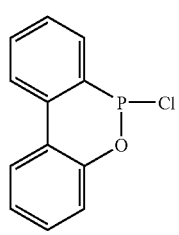

(b) reacting polyhydroxybenzene compound of the formula (III)

$$(HO)_n\text{—Ar} \quad (III)$$

wherein n is 2 or 3; Ar is $C_6$–$C_{16}$ aromatic group, with the compound of formula (II) to form a compound of the following formula (IV)

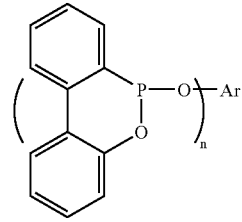

wherein n and Ar are defined the same as the above; and (c) oxidizing the compound of formula (IV) in the presence of water and ozone to form the compound of formula (I).

Method 2

The compound of formula (I) can be prepared by the following steps of (a), (b'), and (c'):

(a) reacting o-phenylphenol with phosphorus trichloride in the presence of zinc chloride catalyst to form a 6-chloro-6H-dibenz [c,e][1,2] oxaphosphorin of the following formula (II);

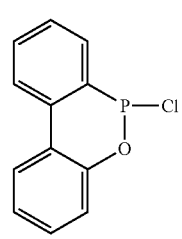

(b') oxidizing the compound of formula (II) in the presence of water and ozone to form a 6-chloro-6-oxide-dibenz [c,e][1,2] oxaphosphorin of the following formula (V); and

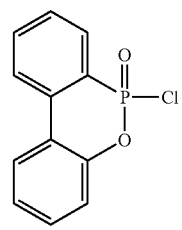

(c') reacting a polyhydroxybenzene compound of the following formula (III)

$$(HO)_n\text{—Ar} \quad (III)$$

wherein, n and Ar are defined the same as the above, with the compound of formula (V) to form the compound of formula (I).

DETAILED DESCRIPTION OF THE PREFERRED EMBODIMENTS

The biphenylphosphonate compound of formula (I)

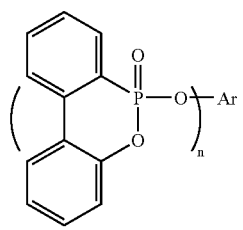

(I)

wherein n is 2 or 3; Ar is $C_6$–$C_{16}$ aromatic group, and Ar is preferably selected from the group consisting of:

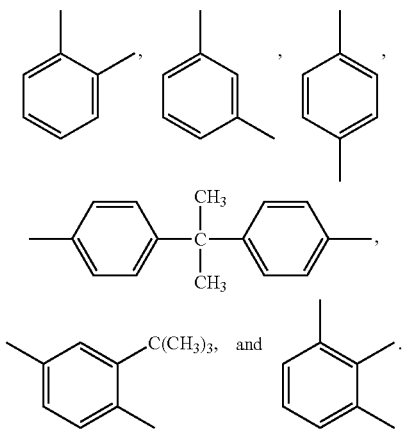

According to the present invention, the preparation of the formula (I) compound is performed in an one-pot reactor. First of all, o-phenylphenol, excessive phosphorous trichloride, and catalystic amount of zinc chloride are mixed together in the reactor with the respective molar ratio of o-phenylphenol to phosphorous trichloride between 1:1 to 1:2. A distillate storage tank equipped with a pressure equilibrium tube and a control valve is installed between the reactor and the condenser. Directly above the condenser a gas inlet is attached, where on the other end of the gas inlet is a drying pipe and it further connects to a neutralization tank. The heating temperature of the first stage of esterification reaction is at the range between 30~200° C. and under normal pressure. After an hour later, the first stage esterification is substantially established where then the thermodynamic trans-esterification and the cyclization reaction are followed afterward (the reaction scheme is described in scheme (1)). The above reactions are completed approximately 4 hours later. Also $^{31}P$ NMR spectrum was used to ensure that the reaction was completed, excess amount of phosphorus trichloride was removed and collected by distillation at reduced pressure.

The crude product 6-chloro-6H-dibenz [c,e][1,2] oxaphosphorin (CDOP) was then injected into organic solvent containing polyhydroxybenzene compound to perform the second stage of esterification reaction, the molar ratio of polyhydroxybenzene compound to CDOP should be between 1:2 to 1:3 to give the best result; toluene, chlorobenzene, and xylene were the most suitable solvents for this reaction, and the temperature was controlled between 60 to 150° C. The reaction went on for 2 hours under nitrogen as shown in scheme (2); and then small amount of ammonia gas ($NH_3$) was added to keep the solution under basic condition, the product was then filtered and carried on to oxidation by ozone as shown in scheme (3), biphenylphosphonate compound was then obtained after the reaction.

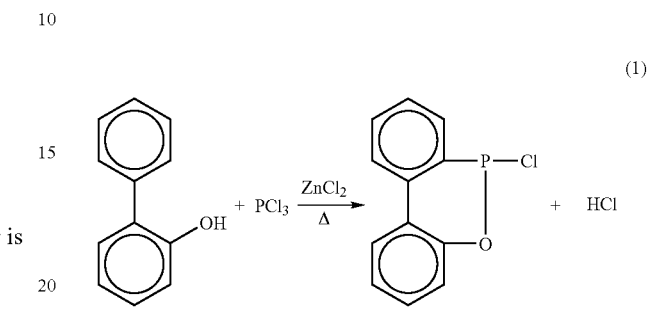

(1)

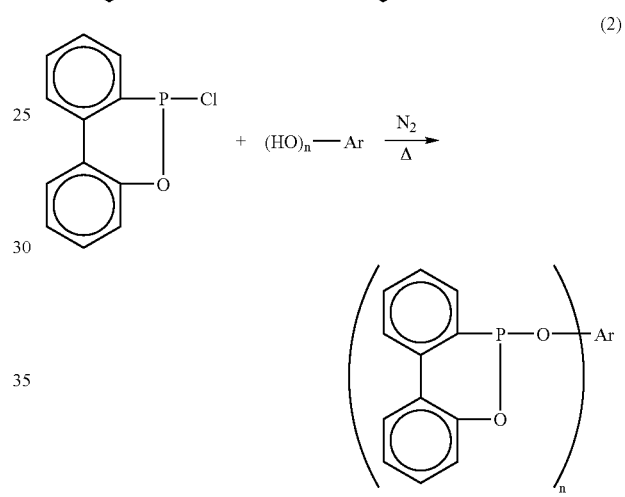

(2)

n = 2, 3

(3)

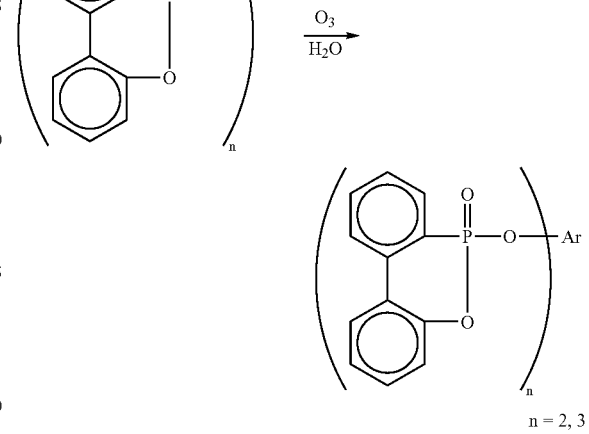

n = 2, 3

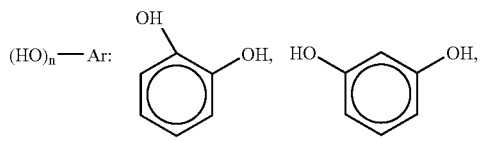

-continued

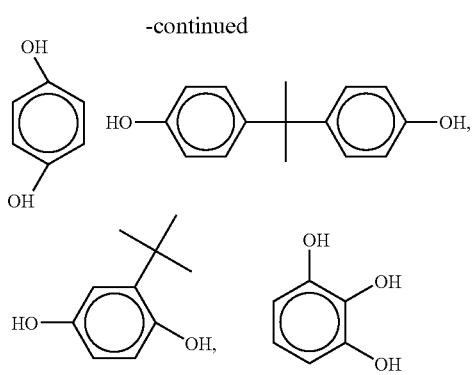

Another reaction route could be achieved by oxidation of CDOP with ozone, obtaining 6-chloro-6-oxide-dibenz [c,e][1,2] oxaphosphorin (CDOPO), as shown in scheme (4); and then esterification with phenols, as shown in scheme (5). In this reaction, the ideal molar ratio of phenols to CDOPO is between 1:2 to 1:3; toluene, chlorobenzene, xylene and etc were the most suitable solvents for this reaction. The esterification reaction was heated to reflux under nitrogen, and the temperature was controlled between 60 to 150° C. During the reaction a base could be added, and organic base works well, especially triethylamine.

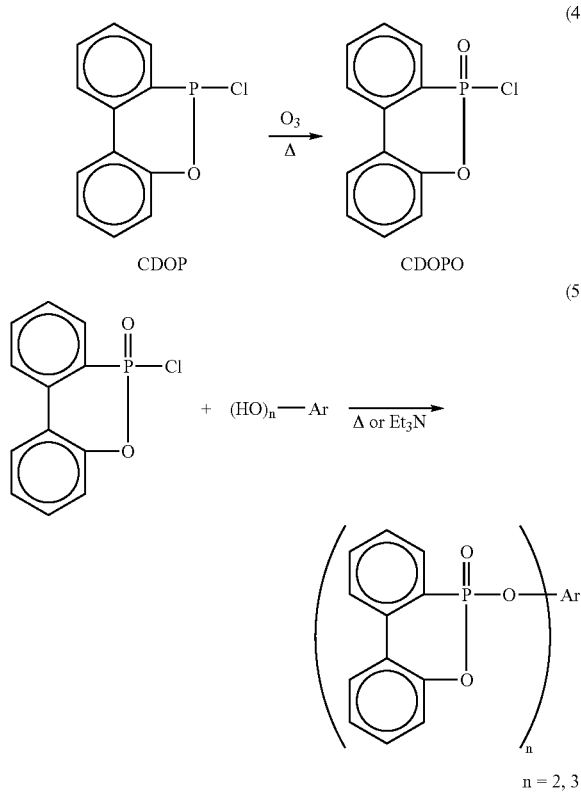

EXAMPLE 1

Add 170 g (1 mol) of o-phenylphenol, 151 g (1.1 mol) of phosphorus trichloride, and 1.36 g (0.01 mol) of zinc chloride into a 2 liter reactor, an addition funnel is set between the reactor and condenser; the condenser pumped with ice water and connected to a neutralizing flask through a air-drying tube. The reaction starts when the temperature is raised to 30° C., and is controlled at 60–80° C.; the rate of generating HCl gas would decrease after one hour, at this stage the major products are single substituded, with small amount of di-substituded product ((Ar'O)$_2$PCl) or tri-substituded product ((Ar'O)$_3$P); Ar'OH stands for o-phenylphenol.

At the second stage of the reaction the temperature is raised and PCl$_3$ is then distilled into the addition funnel above the reactor; when temperature reached 110° C., add PCl$_3$ back into the reaction slowly and heat the reaction to 180° C. for 4 hours, then reaction would stop to generate HCl gas, which shows the reaction is completed. $^{31}$P NMR is also used to check for completion of reaction. After removing excess amount of PCl$_3$ by distillation, CDOP product is then obtained.

The color of reaction described above would change from colorless to yellowish and then to orange color; and then add 55 g (0.5 mol) of resorcinol and 500 ml of toluene into the reaction at room temperature, this is the second esterification. The reaction is then heated to reflux at 110–120° C. and keep stirring for 4 hour, then start to inject N$_2$ bubble into the solution and reflux for 2 hours. The reaction is then cool down to room temperature, then start to inject NH$_3$ bubble into the solution for 5 minutes, orange color side-product and NH$_4$Cl are then filter out and 0.9 g(0.05 mol) of water is added into the solution; then start to inject ozone bubble at a rate of 40 ml/min to the solution and keep stirring for 10 hours. White crystal of 1,3-bis(6-oxo-dibenz[c,e][1,2]oxaphosphorin-6-yl) phenylate, RPO 266 g is obtained after another 16 hours of recrystallation; the overall yield is 98.9%.

EXAMPLE 2~6

The amount of reactants used for the reaction and the condition of the first stage esterification of the present examples are the same as example 1. The second stage esterification reagents and solvents are shown in the following table 1. The reaction conditions and the proceeding oxidation conditions are also the same as example 1, wherein 1,2-bis(6-oxo-dibenz[c,e][1,2]oxaphosphorin-6-yl) phenylate (CPO), 1,4-bis(6-oxo-dibenz[c,e][1,2]oxaphosphorin-6-yl) phenylate (HPO), 3-t-butyl-1,4-bis(6-oxo-dibenz[c,e][1,2]oxaphosphorin-6-yl)phenylate (TPO), 4,4'-bis(6-oxo-dibenz[c,e][1,2]oxaphosphorin-6-yl)-isopropylidenediphenylate (BPO), and 1,2,3-tris(6-oxo-dibenz[c,e][1,2]oxaphosphorin-6-yl) phenylate (PPO) are obtained and shown in table 1.

TABLE 1

| Example | Second stage esterification | Solvent | Yield |
| --- | --- | --- | --- |
| 2 | Catechol 55 g | Toluene 800 mL | 94.8% (CPO) |
| 3 | Hydroquinone 55 g | Chlorobenzene 500 mL | 78.8% (HPO) |
| 4 | t-Butylhydroquinone 83 g | Toluene 500 mL | 96.0% (TPO) |
| 5 | Bisphenol A 114 g | Toluene 500 mL | 97.5% (BPO) |
| 6 | 1,2,3-Trihydroxybenzene 42 g | Xylene 500 mL | 61.7% (PPO) |

EXAMPLE 7

The method for preparing CDOP of the present example is the same as example 1; dissolve the initial product of CDOP in 500 mL of toluene, and then it is settled for 4 hours followed by filtering out the orange byproduct; obtaining 50 mL of the filtrate solution, start to inject ozone bubble into the solution at a rate of 100 ml/min for 6 hours, yellowish solution of CDOPO is then obtained and $^{31}$P NMR is used to check the sample.

EXAMPLE 8~13

Added benzenediol and benzenetriol to the CDOPO solution obtained from example 7 according to the equivalent used in examples 1 through 6, the mixture is then heated to reflux(110–120° C.) to undergo the second stage of esterification, then nitrogen bubble is inject into the solution for 2 hours. Reaction yield is determined by $^{31}$P NMR spectrum: CPO (76.2%) RPO (81.6%) HPO (42.3%) TPO (82.4%) BPO (85.2%) PPO (36.4%).

EXAMPLE 14~19

Added benzenediol and benzenetriol to the CDOPO solution obtained from example 7 according to the equivalent used in examples 1 through 6, 1.05 mol of triethylamine is then added to the mixture at room temperature to start the esterification reaction, after stirring for 2 hours, triethylamine hydrochloride salt is filtered out. $^{31}$P NMR is used to check for completion of reaction. Then the residue is washed with 500 nm of water twice; the reaction yield is determined after removing solvent: CPO (92.5%) RPO (96.6%) HPO (75.7%) TPO (98.7%) BPO (98.5%) PPO (88.2%).

EXAMPLE 20

Wash the BPO solution in toluene obtained from example 5 with 2% NaOH (aq) solution twice, and then remove the solvent by distillation. The BPO product is then been examined by element analysis and the amount of remaining ZnCl$_2$ is under 100 ppm.

A comparison table is shown by following table 2 between the yield of biphenylphosphonate compound from present invention and the Taiwan Patent No. 143,835:

TABLE 2

| Compound | Patent 143835 | Examples 1~6 | Examples 8~13 | Examples 14~19 |
| --- | --- | --- | --- | --- |
| CPO | 69.1% | 94.8% | 76.2% | 92.5% |
| RPO | 78.8% | 98.9% | 81.6% | 96.6% |
| HPO | 29.0% | 78.8% | 42.3% | 75.7% |
| TPO | 78.1% | 96.0% | 82.4% | 98.7% |
| BPO | 79.3% | 97.5% | 85.2% | 98.5% |
| PPO | 78% (Purity) | 61.7% | 36.4% | 88.2% |

As shown in table 2, it is obvious to see that present invention provides methods of preparing biphenylphosphonate compounds with better yield than the Taiwan Patent No. 143,835. Reaction yield is lower (examples 8~13) if CDOP is first oxidized to CDOPO and the second stage esterification reaction is carried out by heating. However, the yield could be easily improved by room temperature condition with the addition of triethylamine (examples 14~19).

A series of biphenylphosphonate compound can be obtained from present invention with higher yield, enrich purity, and facile procedure utilizing nitrogen gas, ammonia gas, and ozone to complete both esterification and oxidation reactions. The intermediate, CDOP from the first stage reacts with polyhydroxybenzene under reflux and nitrogen bubble injecting condition to carry out esterification reaction; cooling down to room temperature the solution is kept basic by injecting small amount of ammonia gas, and after orange colloid and ammonium chloride are filtered, oxidation is carried out using ozone with small amount of water, the crude product can be purified by recrystallation or extraction with NaOH(aq) solution. The intermediate CDOP can also be first oxidized by ozone to give CDOPO, and then carry out esterification with polyhydroxybenzene. The whole procedure can be carried out in one-pot utilizing three kinds of gas reagent to simplify the process and increase the yield, which is highly valuable for economic reason.

Although the present invention has been explained in relation to its preferred embodiment, it is to be understood that many other possible modifications and variations can be made without departing from the scope of the invention as hereinafter claimed.

What is claimed is:

1. A method for preparing a biphenylphosphonate compound of the following formula (I):

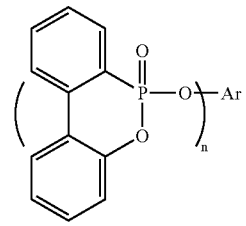

(I)

wherein n is 2 or 3; and Ar is a $C_6$–$C_{16}$ aromatic group; comprising:
 (a) reacting o-phenylphenol with phosphorus trichloride in the presence of zinc chloride catalyst to form 6-chloro-6H-dibenz [c,e][1,2] oxaphosphorin of the following formula (II);

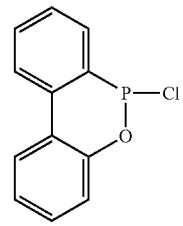

(II)

(b) reacting a polyhydroxybenzene compound of the formula (III)

(HO)$_n$—Ar  (III)

wherein n and Ar are defined the same as the above, with the compound of formula (II) to form a compound of the following formula (IV)

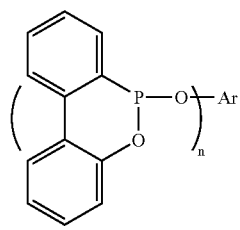

(IV)

wherein n and Ar are defined the same as the above; and (c) oxidizing the compound of formula (IV) in the presence of water and ozone to form the compound of formula (I).

2. The method according to claim 1, wherein the Ar is selected from the group consisting of:

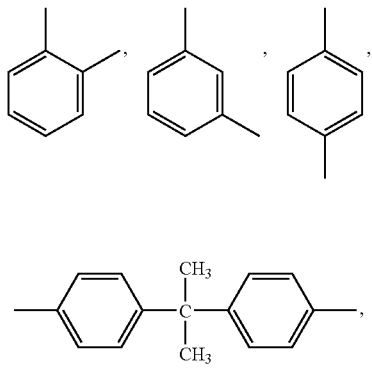

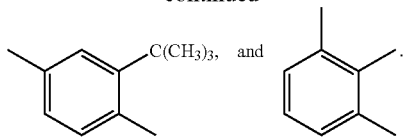

3. The method according to claim 1, wherein the molar ratio of o-benzylphenol to phosphorous trichloride in step (a) is between 1:1 to 1:2.

4. The method according to claim 1, wherein the molar ratio of the compound of formula (III) to the compound of formula (II) in step (b) is between 1:2 to 1:3.

5. The method according to claim 1, wherein the molar ratio of water to the compound of formula (II) in step (c) is between 1:20 to 1:5.

6. The method according to claim 1, wherein the reaction in step (a) is under a temperature between 30° C. to 200° C.

7. The method according to claim 1, wherein the reaction in step (b) is under a temperature between 60° C. to 150° C.

* * * * *